United States Patent [19]
Quinn et al.

[11] Patent Number: 5,966,423
[45] Date of Patent: Oct. 12, 1999

[54] ARC DIFFRACTOMETER

[75] Inventors: Duncan R. Quinn, Budd Lake, N.J.; Fredericus Kerstens, Middletown, N.Y.

[73] Assignee: Philips Electronics North America Corporation, New York, N.Y.

[21] Appl. No.: 08/828,466

[22] Filed: Mar. 28, 1997

[51] Int. Cl.⁶ ........................................... G01N 23/20
[52] U.S. Cl. ................................. 378/81; 378/79
[58] Field of Search ............................ 378/70, 71, 73, 378/79, 80, 87

[56] References Cited

U.S. PATENT DOCUMENTS

| | | | |
|---|---|---|---|
| 2,991,362 | 7/1961 | Schumacher | 250/51.5 |
| 3,218,458 | 11/1965 | Furnas, Jr. | 378/81 X |
| 3,816,747 | 6/1974 | Kishino | 378/73 |
| 3,868,506 | 2/1975 | Ogiso et al. | 250/278 |
| 4,412,345 | 10/1983 | Workman et al. | 378/81 X |
| 5,155,751 | 10/1992 | Chohata et al. | 378/71 |
| 5,187,729 | 2/1993 | Ibe et al. | 378/73 |

FOREIGN PATENT DOCUMENTS

| | | |
|---|---|---|
| 0044492B1 | 1/1982 | European Pat. Off. . |
| 1390710 | 4/1995 | United Kingdom . |

*Primary Examiner*—David P. Porta
*Attorney, Agent, or Firm*—Anne E. Barschall

[57] ABSTRACT

An x-ray diffractometer has an x-ray detector and an x-ray source mounted on vehicles traveling along an arc-shaped track around a sample. The vehicles move independently. Alternatively, the vehicles can move independently on separate parallel tracks.

11 Claims, 5 Drawing Sheets

ARC DIFFRACTOMETER

BACKGROUND OF THE INVENTION

1. Field of the Invention

The invention relates to the field of x-ray diffractometers.

2. Related Art

In x-ray diffractometry, it is desired to measure diffracted x-radiation from a sample. Incident radiation is provided within a measurement plane at an incident angle, omega. Diffracted radiation is observed in the measurement plane at an output angle, referred to herein as 2theta. The values of omega and 2theta depend on the nature of the sample which is to be subjected to the x-radiation.

In the prior art goniometer-based system, see FIG. 1, the source 101 and the detector 102 were carried on arms 103 and 104 attached like the hands of a clock to concentric axles. The source and detector protruded forward from the arms to effect measurements on a sample carried by a platform disposed in front of the concentric axles. In the prior art system, large samples could not be placed on the platform 105, without hitting the arms. Large samples are currently thought of as being as much as 25 cm, though in the future even larger samples might well need to be subjected to x-ray diffraction. The prior art system could not be readily enlarged to accommodate large samples because the longer arms and larger forward extending protrusions for carrying the source and detector were too susceptible to vibration and bending to allow accurate measurements.

SUMMARY OF THE INVENTION

In the x-ray diffractometer of the invention, an x-ray source is moved in an omega vehicle along an arc-shaped track. The x-ray detector is carried on a track in a 2theta vehicle which moves independently from the first vehicle. Optionally, the vehicles can be on the same track. This structure is mechanically stable when enlarged and allows full range of motion for the detector and source.

GB 1390710 shows an x-ray diffraction instrument in which an x-ray source travels on a trolley along an arc-shaped track. X-ray detectors travel along with the x-ray source on the same trolley. The detectors are placed along a second arc-shaped track attached to the trolley carrying the source. EP 044492 shows a similar structure. While the arcs of these patents bear a superficial resemblance to the track system of the invention, in fact they cannot be used for general x-ray diffraction measurements. In the systems of these patents, 2theta is dependent on omega because the detector tracks ride on the trolley bearing the source. As a result these two-track systems are incapable of sufficient angle difference between the source and the detector for generalized x-ray diffraction measurements. These prior systems can only be used for stress measurements. Also, the dependent track structure would become mechanically unstable if enlarged sufficiently to be used with large samples.

BRIEF DESCRIPTION OF THE DRAWING

The invention will now be described by way of non-limitative example with reference to the following figures.

DETAILED DESCRIPTION OF THE PREFERRED EMBODIMENT

Figure 1:
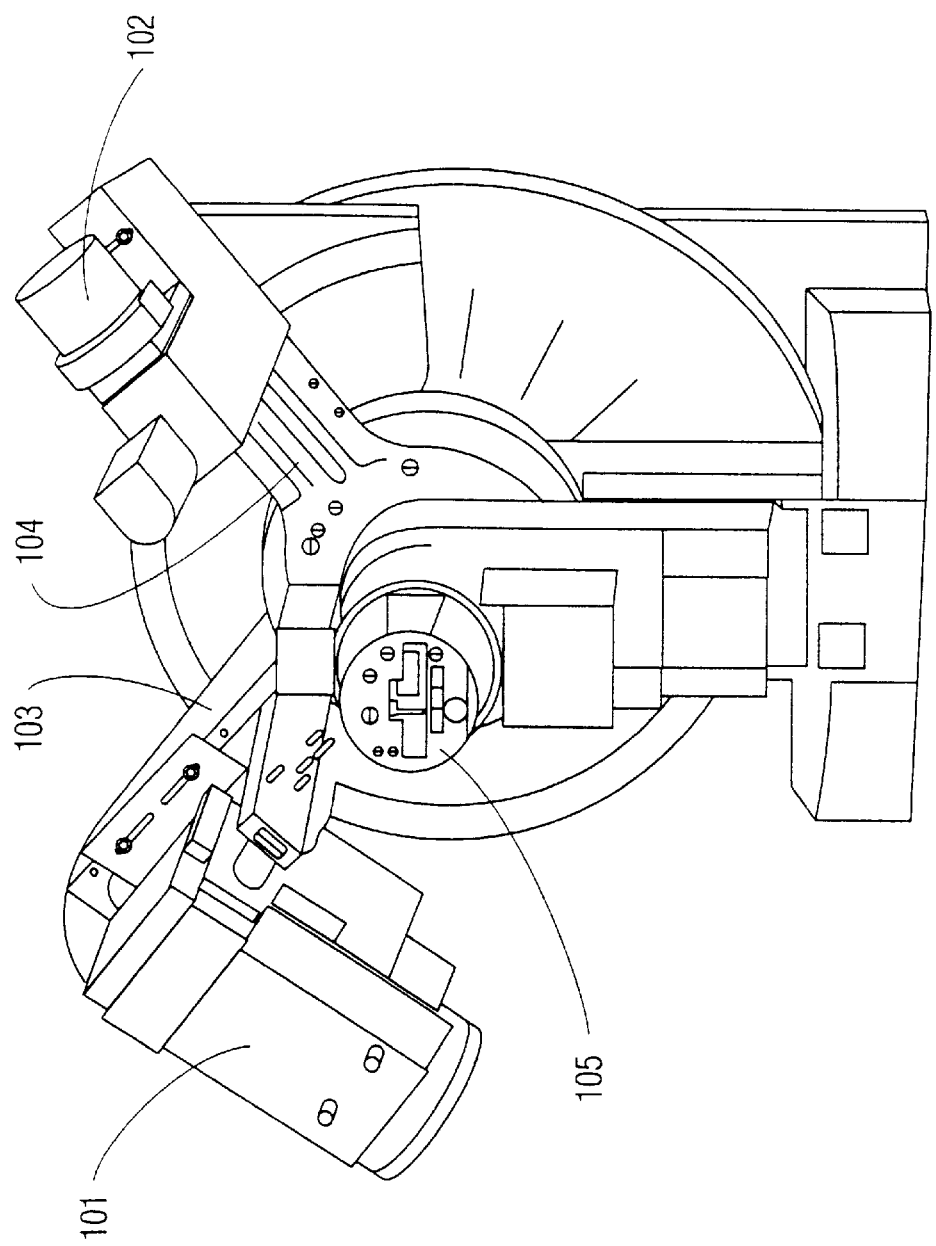
FIG. 1 shows a prior art goniometer-based system
Figure 2:
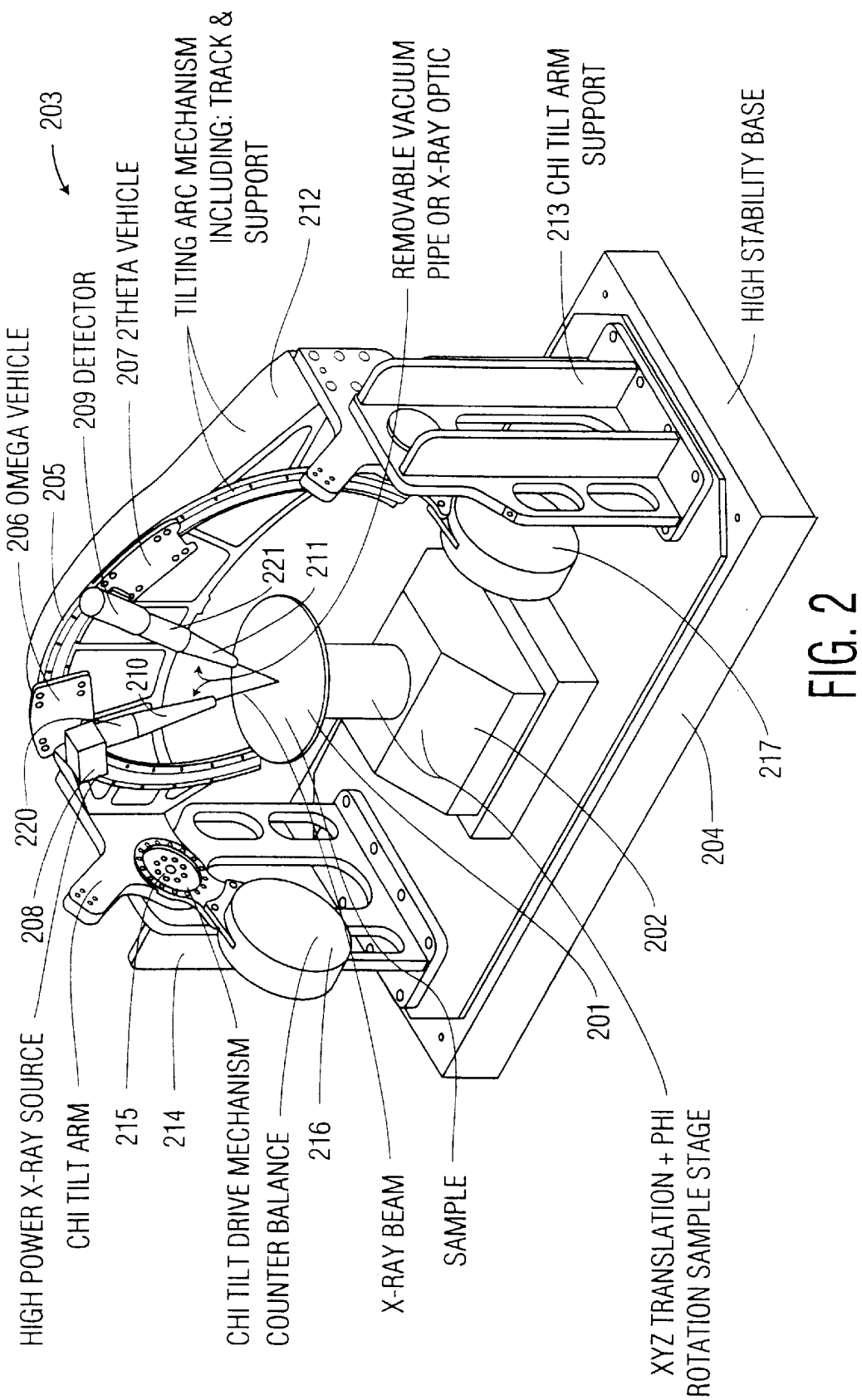
FIG. 2 shows a system in accordance with the invention.

FIG. 2 shows the system of the invention.

The sample rests on a platform 201. The platform rests on a support 202 which has actuators for effecting xyz translation and phi rotation. The sample stage can be adjusted by the skilled artisan to accommodate any desired weight of sample.

Alternatively, the samples can be placed on a conveyor belt that travels through the system along the axis of rotation of the arc 205.

The source/detector mechanism 203 rests on the same base 204 with the sample stage 202. The base needs to have high stability, i.e. giving height variations of less than 0.003" under normal operation. Vibration resistance can be achieved by putting the base on shock absorbing feet. The source/detector mechanism includes an arc 205 carrying an omega vehicle 206 and a 2theta vehicle 207. The arc 205 preferably extends over more than 180° to accommodate the arc size of the vehicles 206 and 207 when at near or past horizontal positions, though a smaller arc could also be used. The arc mechanism can be implemented as a (partial) circular precision track.

The track needs a guidance mechanism for the vehicles. Those of ordinary skill in the art might devise any number of load bearing guidance mechanisms. Examples of guidance mechanisms include 1) an internal or external V groove for guiding V grooved journal wheels on the vehicles; or 2) a rail for guiding slide pads or flat journal wheels on vehicles.

Normally the track would have a drive mechanism for the vehicles, though conceivably the vehicles might contain their own drive mechanism. Those of ordinary skill in the art might devise any number of drive mechanisms. Examples of drive mechanisms include 1) a circular, spur, or worm gear for driving gear wheels on vehicles; or 2) a traction drive rail for driving traction wheels on the vehicles. These drive mechanisms engage structures on the vehicles. Those structures are adjacent to those portions of the guidance mechanisms which are positioned on the vehicles. The guidance mechanisms are described above.

Preferably, the track contains a position encoding mechanism. Those of ordinary skill in the art again might devise any number of position encoding mechanisms. An example of a position encoding mechanism is an optical or magnetic encoding strip.

The guiding, drive, and encoding mechanisms are preferably concentric to obtain improved precision and resolution.

The arc mechanism has a large radius, e.g. a source to sample distance of more than 500 mm. As a result there is a large unobstructed space around the center of the diffractometer for large samples. The radius of the arc is preferably twice the maximal anticipated size of the sample to allow full xy travel of the sample. Samples which are less than or equal to half the radius of the arc can assume arbitrary analysis positions. Larger samples are more constrained in their movements.

An x-ray source 208 rides on the omega vehicle 206. The source is preferably high power, e.g. >1.5 kW. The x-ray detector 209 rides on the 2theta vehicle 209. The detector and the source are preferably equipped with vacuum pipes 210 and 211. The pipes have beryllium windows at each end. These pipes preserve the x-ray energy which would otherwise be dissipated when traveling through the air to and from the sample. Those of ordinary skill in the art might devise other systems to preserve the x-ray energy such as x-ray lenses or x-ray mirrors. They would alleviate the problem of dissipation by taking the divergent x-ray beam and turning it into a parallel beam. In this way, x-rays which would otherwise be lost could hit the sample and be useful, even though the percentage of x-rays absorbed by the air would be the same as without such systems.

Normally, the vehicles will also include beam conditioners 220 and 221, also called x-ray optics, on both the primary and diffracted beam sides. These conditioners can include slits, which limit the divergence and/or acceptance widths, monochromating analyzer crystals, or other beam conditioners known to those of ordinary skill in the art.

Some beam conditioning devices can also be motorized to support automatic alignment or to switch between different devices,.

The arc 205 is mounted on a support 212. The support may be integral to the track or a separate structure which provides a pilot to the track, the latter being shown in the figures. The combined mechanism provides stability, accuracy, reproducibility and resolution equivalent to the prior art goniometer based x-ray diffractometer. The step size for the vehicles should be no more than 0.001° to give the desired resolution. The accuracy of the omega or 2theta positions after a movement of the vehicles must be better than 0.01°. The reproducibility requirement is that every subsequent return to a same position must yield the same position to within less than 0.001°. Those of ordinary skill in the art can devise mechanisms yielding various other tolerances as required for particular measurements.

The support 212 in turn is mounted on chi tilt arm supports 213 and 214. A chi tilt drive mechanism 215 controls the chi angle of the arc 205. Counter balance weights 216 and 217 give stability. The design of the chi tilt mechanism uses the arc as a bypass of the chi-tilt axle mechanism to avoid interference with the sample. In other words the axle is split in two sections separated and held together by the arc.

Figure 3:
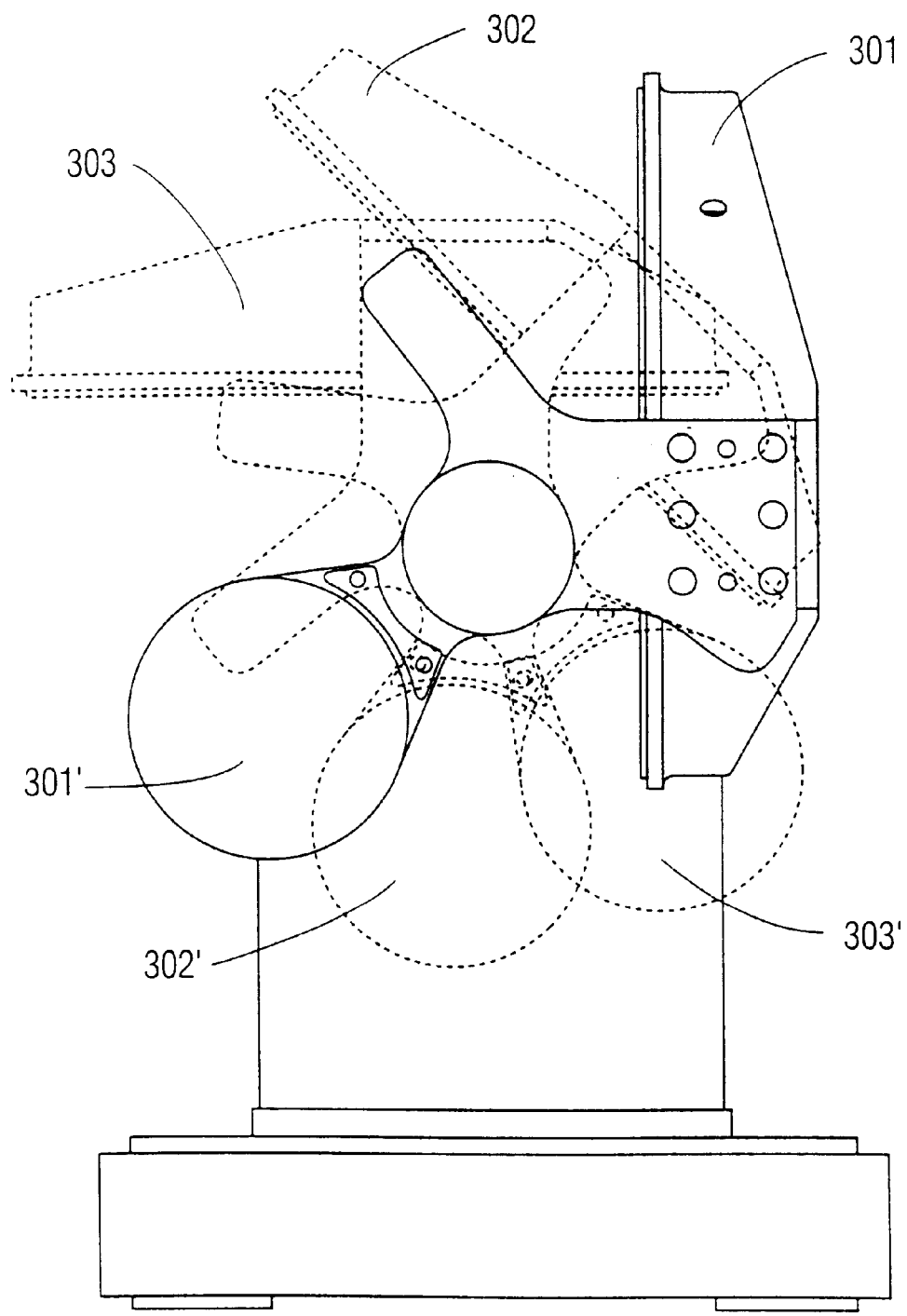
FIG. 3 shows a side view of the system of FIG. 2, showing the chi tilt mechanism.

FIG. 3 shows a side view of the system in accordance with the invention. Three possible chi angles of the system are shown. The vertical position of the arc/support mechanism 301 is shown in solid lines. The tipped 302 and horizontal 303 positions are shown in dotted lines. The counter weights move along with the arc/support system to positions 301', 302', and 303', corresponding to the positions 301, 302, and 303, respectively.

Figure 4:
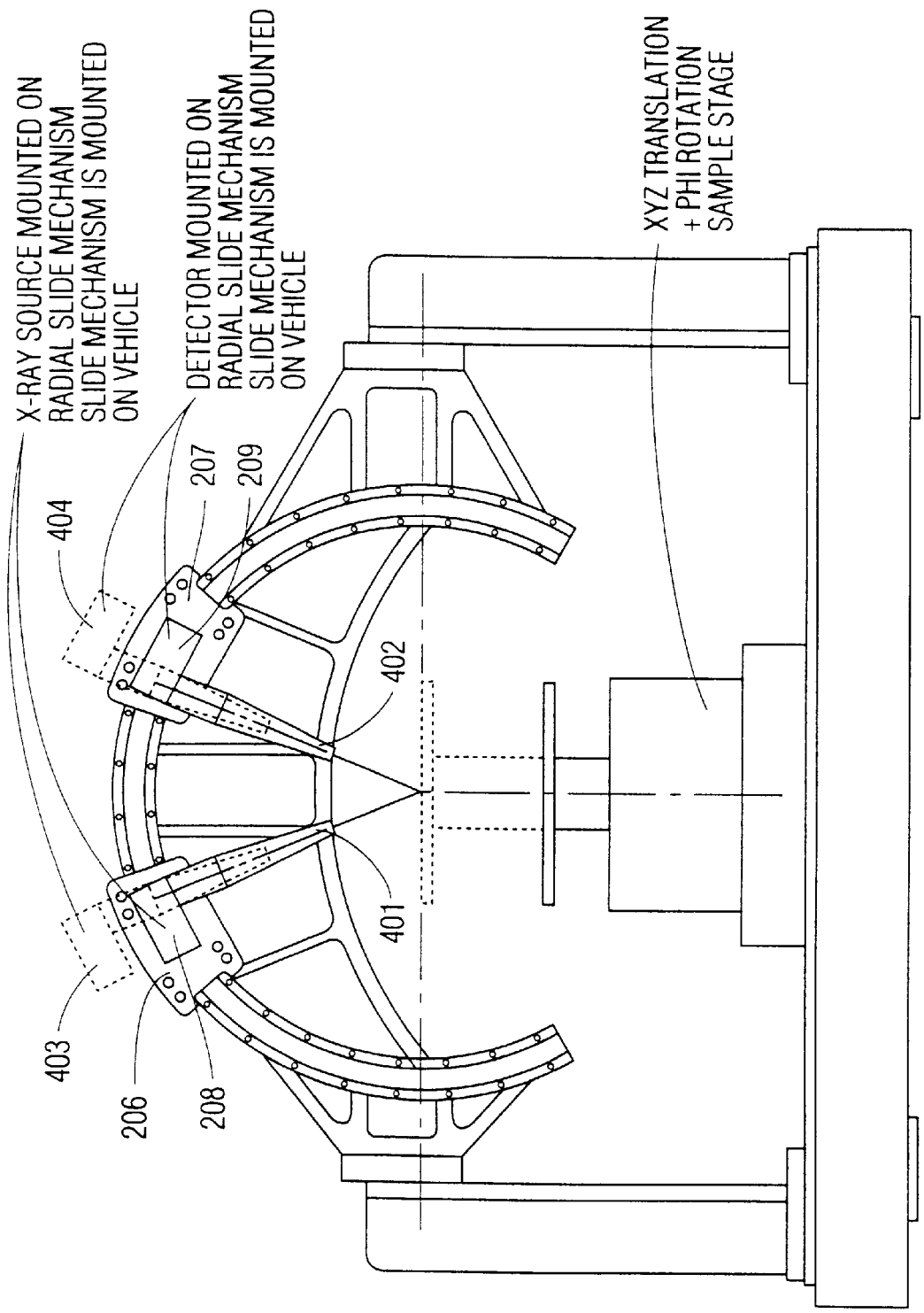
FIG. 4 shows a variable radius alternate embodiment of the invention.

FIG. 4 shows an alternate embodiment of the invention in which the x-ray source and detector are slidably mounted to the vehicles 206 and 207. The lower positions 401 and 402 are suitable for smaller samples. The raised positions 403 and 404, shown with dotted lines, are suitable for larger samples. Alternatively, the vacuum pipes may be removed for larger samples. To allow for such a possibility the vacuum pipes in FIG. 2 can be removably mounted to the vehicles.

Figure 5:
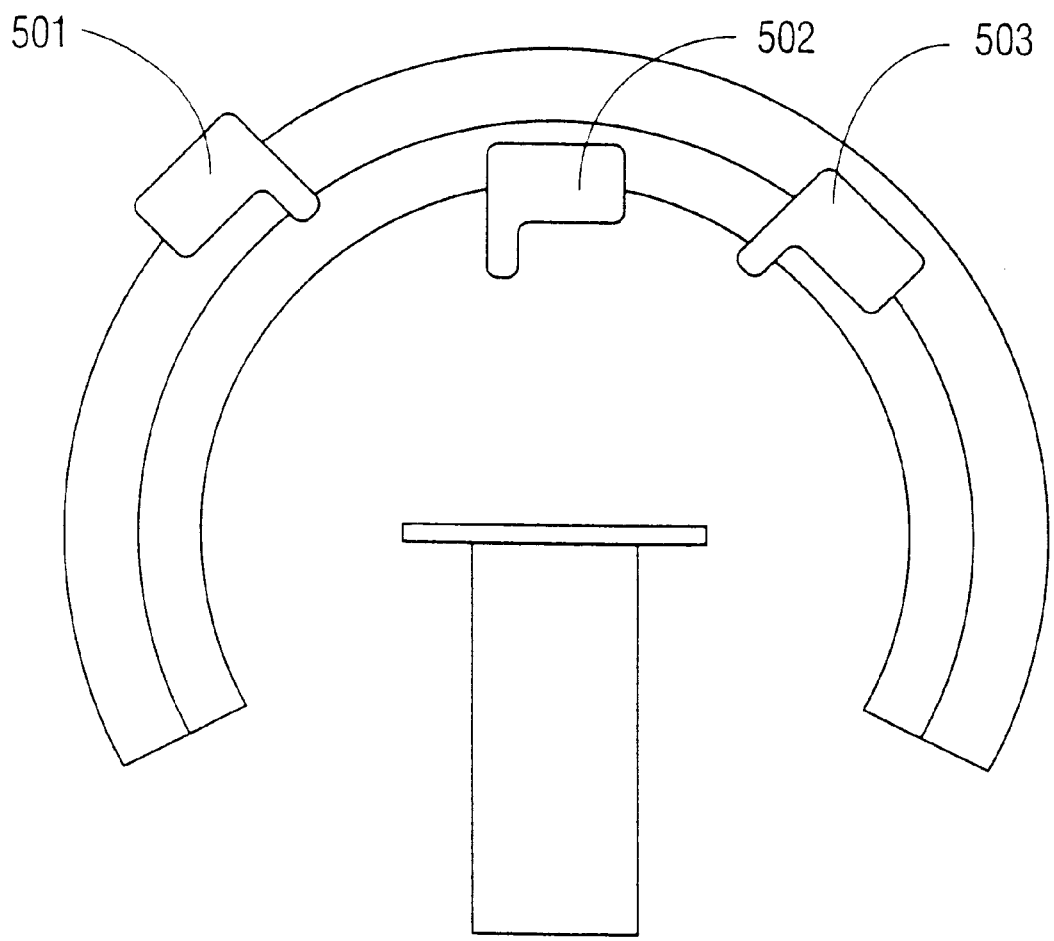
FIG. 5 shows a multiple track alternate embodiment of the invention.

FIG. 5 shows another alternate embodiment. In this embodiment, the source 501 and detectors 502 and 503 travel along separate, concentric tracks mounted on the same support. Since such tracks are completely mechanically separate, the movement of the source and detector vehicles would still be completely independent. Having 2 detectors allows for a greater variety of measurements than a single vehicle allows.

We claim:

1. An x-ray diffractometer comprising
   a. an x-ray source;
   b. an x-ray detector;
   c. at least one arc-shaped track;
   d. a source vehicle for carrying the x-ray source along the at least one arc-shaped track;
   e. a detector vehicle for carrying the x-ray detector along the at least one arc-shaped track, the detector vehicle moving independently from the source vehicles
   f. a chi tilt mechanism for tilting the arc-shaped track; wherein
      the track subtends an angle of greater than 180°; and
      the chi-tilt mechanism is arranged to achieve a chi-tilt near or past horizontal.

2. The diffractometer of claim 1 wherein there is only a single track and the source and detector vehicles both travel along the single track.

3. The diffractometer of claim 1 further comprising first and second vacuum pipes mounted on the x-ray source and x-ray detector, respectively.

4. An x-ray diffractometer comprising
   a. an x-ray source;
   b. an x-ray detector;
   c. at least one arc-shaped track;
   d. a source vehicle for carrying the x-ray source along the at least one arc-shaped track; and
   e. a detector vehicle for carrying the x-ray detector along the at least one arc-shaped track, the detector vehicle moving independently from the source vehicle,
   wherein the x-ray source and the x-ray detector are slidably mounted on their respective vehicles so that the source and detector are movable in a radial direction with respect to an axis of the arc of the at least one arc-shaped track.

5. The diffractometer of claim 4 further comprising first and second vacuum pipes mounted on the x-ray source and x-ray detector, respectively.

6. The diffractometer of claim 4 further comprising a chi-tilt mechanism for tilting the arc-shaped track.

7. An x-ray diffractometer comprising
   a. an x-ray source;
   b. an x-ray detector;
   c. at least one arc-shaped track;
   d. a source vehicle for carrying the x-ray source along the at least one arc-shaped track; and
   e. a detector vehicle for carrying the x-ray detector along the at least one arc-shaped track, the detector vehicle moving independently from the source vehicle
   wherein the at least one arc-shaped track comprises first and second concentric arc shaped tracks, with the source vehicle movably mounted to move along the first track and the detector movably mounted to move along the second track.

8. The diffractometer of claim 7 wherein the at least one arc-shaped track comprises a third concentric arc shaped track with a second detector vehicle carrying a second detector movably mounted to move along the third track.

9. The diffractometer of claim 7 further comprising first and second vacuum pipes mounted on the x-ray source and x-ray detector, respectively.

10. The diffractometer of claim 7 further comprising a chi tilt mechanism for tilting the arc-shaped track.

11. The diffractometer of claim 7, wherein the x-ray source and the x-ray detector are slidably mounted on their respective vehicles so that the source and detector are movable in a radial direction with respect to an axis of the arc of the at least one arc-shaped track.

* * * * *